Figure 1:
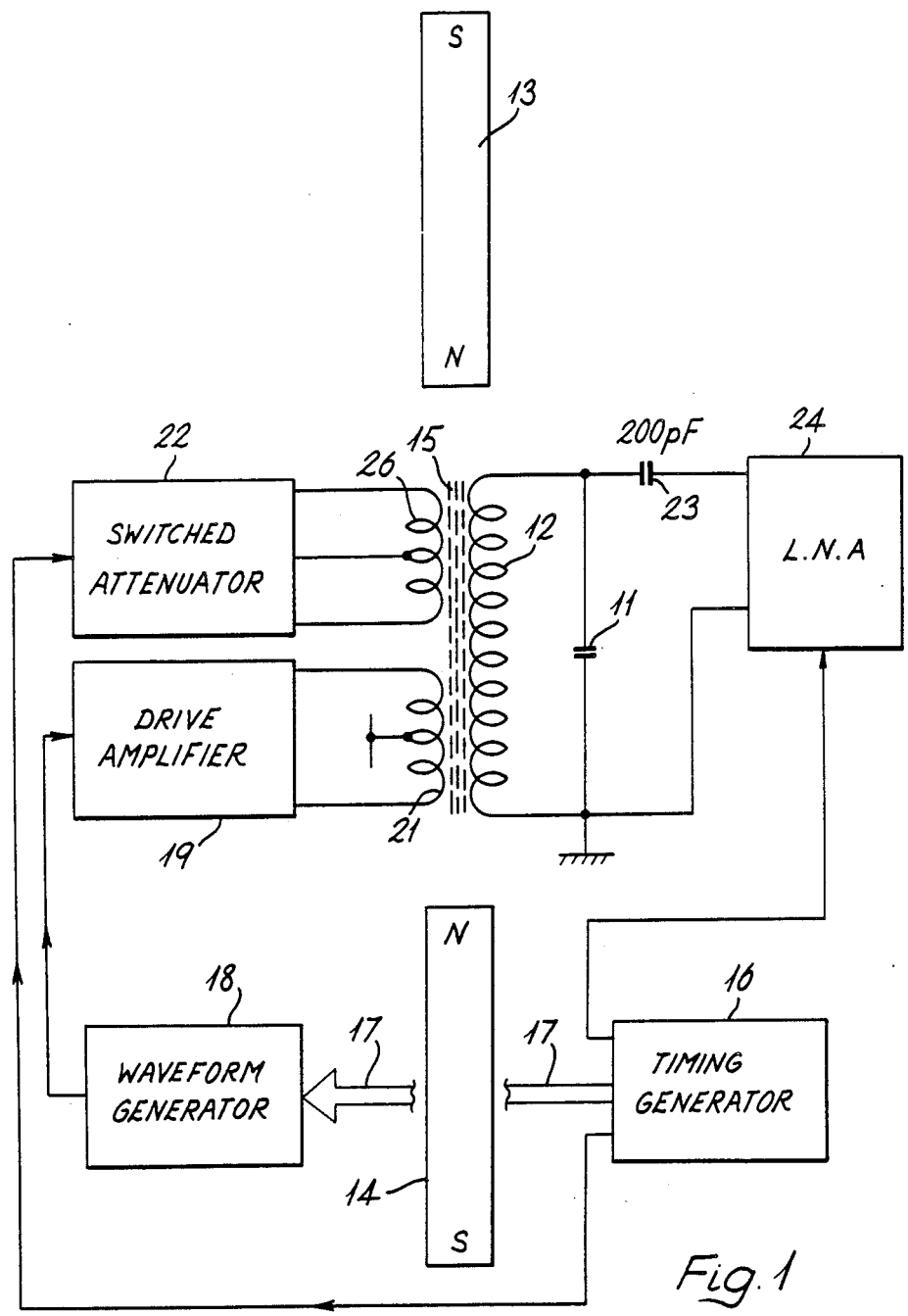

United States Patent [19]

Willard et al.

[11] Patent Number: 4,706,030

[45] Date of Patent: Nov. 10, 1987

[54] WAVEFORM GENERATOR FOR NUCLEAR MAGNETIC RESONANCE APPARATUS

[75] Inventors: Reginald A. Willard, Middlesex; William S. Percival, London, both of England

[73] Assignee: National Research Development Corporation, London, England

[21] Appl. No.: 857,309

[22] Filed: Apr. 30, 1986

[30] Foreign Application Priority Data

May 3, 1985 [GB] United Kingdom ............... 8511382
May 3, 1985 [GB] United Kingdom ............... 8511354

[51] Int. Cl.$^4$ .......................................... G01R 33/20
[52] U.S. Cl. .................................. 324/322; 324/303; 307/262; 307/555; 328/223
[58] Field of Search ............... 324/303, 309, 314, 318, 324/322, 306; 307/262, 264, 362, 540, 555, 556; 328/113, 223

[56] References Cited

U.S. PATENT DOCUMENTS

| | | | |
|---|---|---|---|
| 2,527,474 | 10/1950 | Alvarez | 328/323 |
| 3,239,763 | 3/1966 | Cistola | 328/323 |
| 3,617,867 | 11/1971 | Herzog | 324/303 |
| 3,763,478 | 10/1973 | Yoshizawa et al. | 328/113 |
| 3,768,003 | 10/1973 | Amen | 324/311 |
| 4,350,955 | 9/1982 | Jackson et al. | 324/303 |
| 4,565,968 | 1/1986 | Macovski | 324/306 |
| 4,629,986 | 12/1986 | Clow et al. | 324/303 |
| 4,654,591 | 3/1987 | Moran | 324/306 |

FOREIGN PATENT DOCUMENTS

1557450  12/1979  United Kingdom .
2141236  12/1984  United Kingdom .

Primary Examiner—Stewart J. Levy
Assistant Examiner—Kevin D. O'Shea
Attorney, Agent, or Firm—Cushman, Darby & Cushman

[57] ABSTRACT

Nuclear magnetic resonance is excited in surrounding fluids by pulsing a first winding which with a capacitor forms a resonant circuit. In order to observe signals induced by NMR in the first winding between pulses, the pulses are given an envelope which rises linearly to a peak and then immediately decays linearly to zero. A waveform generator generates bursts of constant amplitude oscillations having a 180° phase change at the centre of each burst. When such bursts are applied to the resonant circuit by way of a drive amplifier and a second winding wound over the first winding, the required envelope is generated in the first winding.

9 Claims, 7 Drawing Figures

WAVEFORM GENERATOR FOR NUCLEAR MAGNETIC RESONANCE APPARATUS

The present invention relates to a generator for a waveform which when applied to a resonant circuit causes oscillations in the circuit to have a triangular envelope with linear growth and decay. The invention is particularly but not exclusively of use with nuclear magnetic resonance (NMR) apparatus.

As described in UK patent application No. 2141236A an advantageous method of nuclear magnetic borehole logging employs a solenoid disposed between two permanent magnets, the solenoid being pulsed to produce a radiofrequency magnetic field in the region of the coil. One application of the present invention is to generate oscillations in a resonant circuit of which the solenoid forms a part. In this application, the drive signal may have a magnitude of the order of 250 volts but it is required about 500 microseconds after each application of the drive signal to use the solenoid to receive a signal from the protons of water in material surrounding a borehole which may be less than a microvolt. For this purpose the drive voltage must be attenuated by more than $10^{-9}$ in an interval of about 500 microseconds. Attenuation is mainly achieved by a switched attenuator which is described in our co-pending U.S. patent application Ser. No. 857,310 entitled "Resonant Circuit with Switched Attenuator" having the same date as the present application and the same inventors. However the attenuation required of this attenuator is reduced by the present invention.

Apparatus similar to that of the above mentioned patent application may also be employed in other types of cavity or orifice, for example a miniature version may be employed for NMR in the human or animal body.

According to one aspect of the present invention there is provided nuclear magnetic resonance apparatus comprising first and second means for generating opposed magnetic fields in a space containing a solenoidal first winding having its axis aligned with the fields and containing a core of magnetic material, reactive impedance connected across the first winding to form a high Q resonant circuit, waveform-generation means for generating pulses formed by bursts of oscillations and for applying the pulses to the first winding, each pulse having a rectangular envelope and two contiguous portions with a phase change of 180° at the junction of the two portions, means for adjusting the amplitude of one of the portions of each pulse, means for adjusting the duration of the same or the other portion of each pulse, and means for deriving signals representative of signals induced in the first winding between the bursts.

According to another aspect of the present invention there is provided a waveform generator for a high Q resonant circuit to generate in the resonant circuit oscillations having an envelope which rises in magnitude linearly to a maximum and then immediately decays linearly to zero, comprising means for generating pulses formed by bursts of oscillations, each pulse having a rectangular envelope and two contiguous portions with a phase change of 180° at the junction of the two portions, means for adjusting the amplitude of one of the portions of each pulse, and means for adjusting the duration of the same or the other portion of each pulse.

The bursts are preferably bursts of sinusoidal oscillations.

The first portion of each pulse when applied to a high Q resonant circuit generates oscillations in the coil having an envelope which rises substantially linearly and when the second portion follows with its phase reversed, the oscillations decay with the envelope falling substantially linearly.

Using pulses with this envelope in the solenoid of NMR borehole logging equipment provides a drive signal which is relatively near to zero at the end of a pulse and thus aids in attenuating the drive signal before NMR signals are received.

An important feature of the invention is that the linear decay of the envelope waveform can be adjusted so that it continues substantially linearly to zero. This is achieved by observing the waveform and using the means for adjusting amplitude and duration to ensure linear decay to zero. The process is more easily achieved if it is the amplitude and duration of the second portion of each pulse which is adjustable. Using one form of the invention it is possible to reduce the amplitude at the end of each pulse in the resonant circuit to less than 1% of the peak amplitude and in the example given the voltage is reduced to less than 1 volt.

Figure 2:
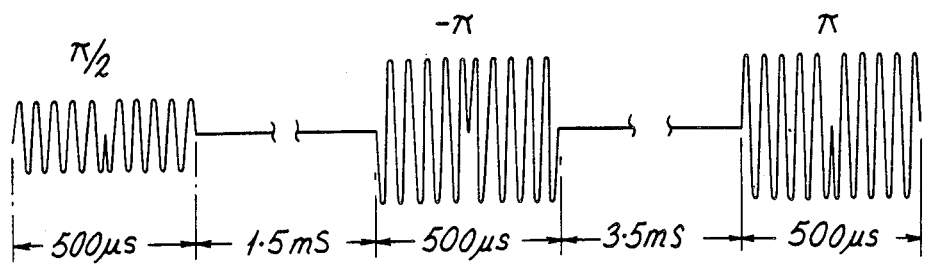
Figure 3:
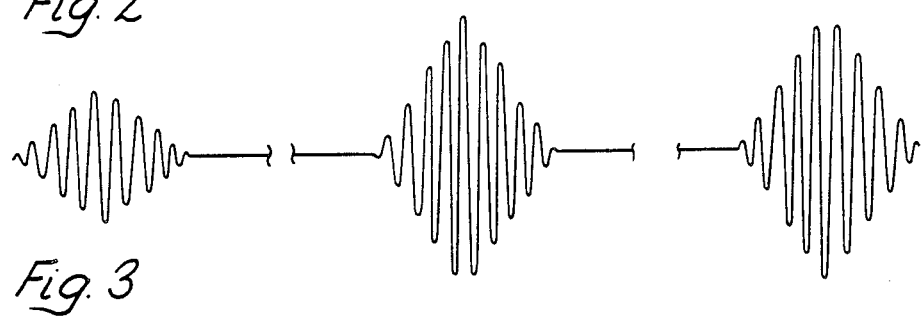
Figure 4:
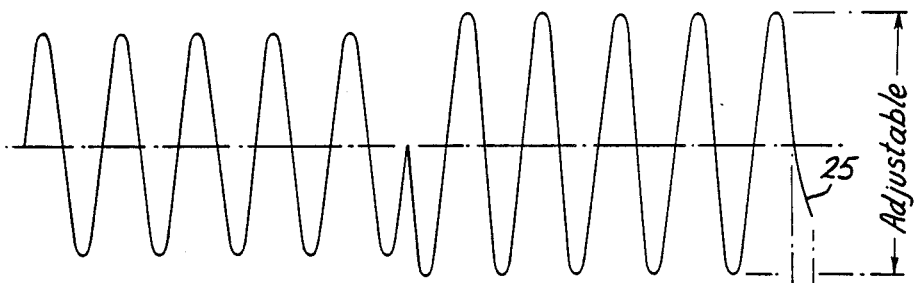
Figure 5:
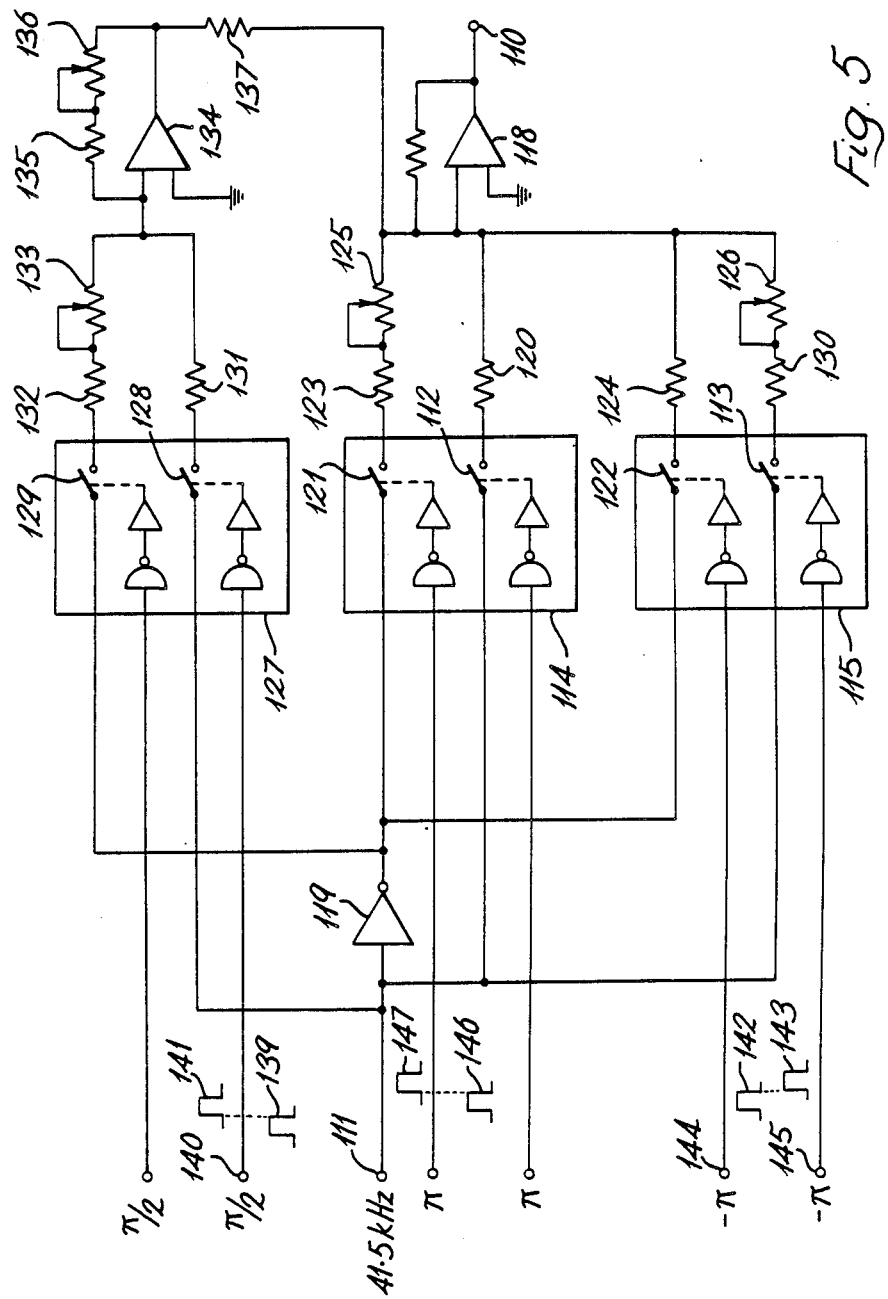
Figure 6:
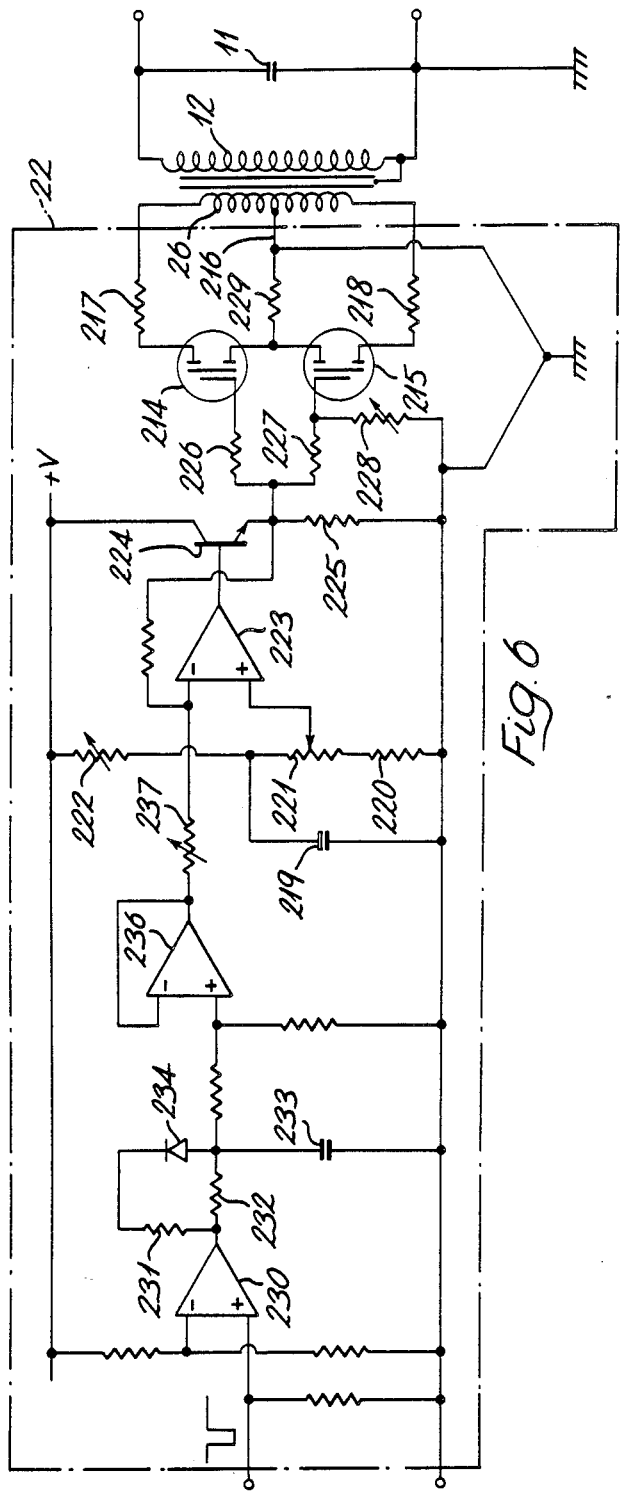
Figure 7:
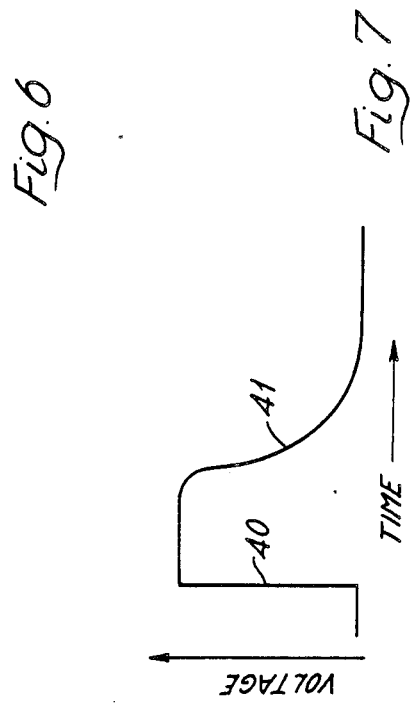

An embodiment of the invention will now be described by way of example with reference to the accompanying drawings, in which:

FIG. 1 is a block diagram of NMR apparatus employing the invention,

FIG. 2 shows pulses generated by a waveform generator according to the invention, FIG. 3 shows pulses in a high Q resonant circuit resulting from the pulses of FIG. 2, FIG. 4 shows one of the pulses of FIG. 2 in more detail, FIG. 5 is a block diagram of a waveform generator according to the invention, FIG. 6 is a diagram of the switched attenuator of FIG. 1, and FIG. 7 shows the waveform of a switching pulse employed in the circuit of FIG. 6.

An NMR system employing the invention is first described. In FIG. 1 a capacitor 11, a winding 12 in the form of a solenoid, two permanent magnets 13 and 14, and a core 15 (for the winding 12) of high permeability ferrimagnetic material are arranged to function in the way described in the above mentioned British patent application No. 2141236A. However as mentioned above the apparatus, perhaps modified in size, may be employed for other NMR applications. The magnets, the winding 12 and its core and much, or all, of the electronics shown in FIG. 1 are positioned in a cylindrical housing (not shown) which, in use, is for example lowered down a borehole, or inserted into a body cavity.

A timing generator 16 provides a sequence of pulses along a bus 17 to cause a waveform generator 18 to generate a series of pulses of the form shown in FIG. 2 as input signals for a balanced drive amplifier 19 feeding a winding 21 wound over the winding 12. The winding 21 induces waveform pulses in the winding 12 which excite NMR in a fluid (such as water or oil) in a geological formation surrounding a borehole, or in body tissue surrounding a cavity. The waveform generator is described in more detail below. The waveform induced in the resonant circuit formed by the winding 12 and the capacitor 11 is as shown in FIG. 3 and at the end of each burst of oscillations forming a pulse, any residual voltage is attenuated by a switched attenuator 22 coupled to a winding 26 wound over the winding 12. The attenuator 22 is described in more detail below. In the intervals between the bursts of oscillations when the exciting voltage has decayed and been attenuated sufficiently NMR signals are picked up by the winding 12 and passed by way of a capacitor 23 to a low noise amplifier 24. Limiting diodes (not shown) are connected at the input to the amplifier to reduce the drive voltage during the bursts of oscillations of FIG. 3. One or more F.E.T. shorting switches (not shown) may also be included in the amplifier and operated by the timing generator 16 to be closed while the drive voltage is present.

The pulses (formed by bursts of oscillations) in FIG. 3 have the general form of the Carr-Purcell sequence which is known for use in nuclear magnetic resonance (NMR). However, the pulses shown differ from the normal Carr-Purcell sequence in that there is a 180° phase change at the centre of each pulse. As is usual the sequence starts with a half amplitude pulse designated $\pi/2$ and is then followed by full amplitude pulses of alternating phase starting with a pulse of opposite phase to the $\pi/2$ pulse. In view of the change of phase at the beginning of each pulse the following pulses are known as $-\pi$ and $\pi$ pulses, alternately. $\pi$ and $-\pi$ pulses are, in this example, separated by intervals of approximately 4 milliseconds (from start to start) while the initial interval between the $\pi/2$ pulse and the first $-\pi$ pulse is approximately 2 milliseconds (from start to start). Each $\pi/2$ pulse, $-\pi$ and $\pi$ pulse has a duration of approximately 500 microseconds.

When the first half of one of the pulses of FIG. 2 is applied to a high Q resonant circuit such as that used in an NMR borehole logging device of the type mentioned above where the resonant circuit includes a solenoid positioned between two permanent magnets, the result is a linear growth in amplitude of oscillations in the solenoid, provided the frequency of the sinusoidal waveform is equal to or near the resonant frequency of the resonant circuit. The linear growth in amplitude is followed by a linear decay starting when the phase change of 180° occurs. Such pulses in a resonant circuit are shown in FIG. 3.

At the peak of the envelope of FIG. 3 in a $\pi$ or $-\pi$ pulse the amplitude of the voltage waveform is of the order of 250 volts and it is required that the envelope decays linearly to zero volts. This is achieved by making each $\pi$ or $-\pi$ pulse in the form shown in FIG. 4 where the first portion is of constant duration and constant amplitude but the second portion is of adjustable amplitude and duration. In setting up the apparatus the waveform across the resonant circuit is observed, for example using an oscilloscope, and the second half of each pulse is adjusted to give the required linear decay to zero. Thus a portion 25 can be advanced (as shown) or retarded beyond the position where the signal would finish at a cross-over point so that the second half of each pulse can be made, with the assistance of the amplitude adjustment, to "cancel" each first half as exactly as possible so that the sinusoidal waveform in each pulse finishes as near to zero as possible. The first half of each pulse of FIG. 4 consists of 5 to 10 sinusoidal oscillations, as does the second half.

The waveform of FIG. 4 in the pulse sequence of FIG. 2 appears at an output terminal 110 of FIG. 5 and is formed by switching a sinusoidal waveform applied at an input terminal 111 without inversion and by way of an inverting amplifier 119, alternately. For NMR, the waveform applied at the terminal 111 is at the Larmor frequency which depends on the magnetic field generated and the material subjected to the field. As an example the Larmor frequency is taken to be 14.5 kHz. In order to generate the first half of $\pi$ bursts and the second half of $-\pi$ bursts, the input terminal 111 is connected by way of contacts 112 and 113 in dual analogue switches 114 and 115 and resistors 120 and 130, respectively, to the input of a summing amplifier 118. A variable resistor 126 is connected between the resistor 130 and the amplifier 118. The second half of each $\pi$ burst and the first half of each $-\pi$ burst is obtained by connecting the output of an inverting amplifier 119, connected to the input terminal 111 by way of contacts 121 and 122 and resistors 123 and 124 to the summing amplifier 118. A variable resistor 125 is connected between the resistor 123 and the summing amplifier 118.

Similar connections are provided to generate the $\pi/2$ bursts, using a dual analogue switch 127 with contacts 128 and 129, resistors 131 and 132 and a variable resistor 133. However a variable gain amplifier 134 with fixed and variable resistors 135 and 136 and an output resistor 137 are inserted at the input to the summing amplifier 118.

In operation, a gating pulse 139 is first applied to a terminal 140 generating the first half of the $\pi/2$ pulse by closing the contacts 128 and gating the 41.5 kHz signal to the amplifier 118 and so to the output terminal 110. The second half is obtained by starting a gating pulse 141 concurrently with the end of the pulse 139 to gate a similar but inverted pulse of the 41.5 kHz signal to the amplifier 118 by way of the contacts 129. Thus the required phase change is obtained in the middle of the $\pi/2$ pulses. The variable resistor 136 is used to adjust the amplitude of the $\pi/2$ pulses and the variable resistor 133 is used to adjust the amplitude of the second half of such pulses. Each pulse 139 and 141 has a duration of approximately 250 microseconds.

After an interval of approximately 1.5 milliseconds a gating pulse 142 is applied to a terminal 144, followed immediately by a gating pulse 143 applied to a terminal 145. Inverted and non-inverted cycles of the 41.5 kHz signal reach the output terminal 110 by way of the contacts 122 and 113, respectively, to give $-\pi$ pulses. The variable resistor 126 allows the amplitude of the non-inverted cycles to be adjusted as indicated in FIG. 3. Each pulse 142 and 143 also has a duration of approximately 250 microseconds as do later pulses 146 and 147.

After an interval of approximately 3.5 milliseconds gating pulses 146 and 147 occur switching contacts 112 and 121 successively and generating the $\pi$ pulses, with the amplitude of the inverted portion adjustable by means of the variable resistor 125.

Pulse pairs 142, 143 and 146, 147 are now generated alternately at about 4 millisecond intervals until the end of the exciting Pulse sequence is reached. The $\pi/2$, $-\pi$, $\pi$ sequence is then repeated after a predetermined interval.

The gating pulses 139, 142 and 146 are derived in the timing generator 16 by division from a crystal controlled master oscillator (not shown) and pulses from this oscillator also trigger respective monostable circuits (not shown) which provide the pulses 140, 143 and 147. The monostable circuits are adjustable to give the adjustment 25 of the duration of the second halves of the $\pi$, $-\pi$, and $\pi/2$ pulses. The gating pulses reach the waveform generator 18 by way of the bus 17.

The terminal 110 at the output of the circuit of FIG. 5 is connected by way of the drive amplifier 19 to the winding 21 which has a low Q. The winding 12 has a high Q secondary winding and with the capacitor 11 forms the resonant circuit (in this example resonant at 41.5 kHz) in which the waveform of FIG. 3 appears.

The switched attenuator 22 shown in FIG. 6 is now described. When the oscillations of FIG. 3 in the resonant circuit (the capacitor 11 and the winding 12) decay they are further rapidly attenuated by the switched attenuator 22 connected to the winding 26. The attenuator 22 comprises two MOSFETs 214 and 215 of the depletion type (n or p channel) each with source electrode connected to a centre tap 216 of the winding 26 by way of a resistor 229 typically of value 10 kOhms. Resistors 217 and 218 are connected between opposite ends of the winding 26 and drain terminals of the FETs 214 and 215, respectively. Together the resistors 217 and 218 have a resistance which when added to the resistances of the FETs (often each about 1 Ohm) and referred to the winding 12 equals half the reactance of the inductor formed by the windings 12, 21 and 26 and the core 15 when also referred to the winding 12. As is known, the connection of a resistance of this value across the inductor of a resonant circuit causes attenuation of oscillations in the circuit to occur at the maximum possible rate. In many applications the MOSFETs 214 and 215 may be International Rectifier type IRF 830 or similar, which while conducting have a resistance of about 1 Ohm and the resistors 217 and 218 may then be 1.5 Ohms each assuming that the reactance of the above mentioned inductor referred to the winding 26 is 5 Ohms.

In the absence of a drive signal, the FETs 214 and 215 are biassed to their non-conducting state by a bias voltage derived from a resistor 220 and variable resistors 221 and 222 connected across a positive supply voltage. A capacitor 219 decouples the resistors 220 and 221. The voltage from these resistors is applied by way of an operational amplifier 223, a bipolar transistor 224 with emitter resistor 225 and two equal resistors 226 and 227, typically of value 100 Ohms, in series with the gate electrodes of the respective FETs. Fine and coarse adjustment of the bias voltage is achieved by adjustment of the resistors 221 and 222, respectively, and a variable resistor 228, typically of value 10 kOhms, is connected between the gate of the FET 215 and earth to balance the gate electrodes to earth over the region of the FET characteristics where transition between low and high resistance takes place.

When it is required to attenuate oscillations in the resonant circuit a positive pulse from the timing generator 16 is applied to the transistor 224 switching on both the FETs. The FETs then conduct together passing a rapidly decaying alternating current driven by the voltage across the winding 26. When the FETs are switched to the non-conducting state at the end of the pulse, any transient voltages which appear across the FETs 214 and 215 are in opposition at the primary winding 26 and therefore cancel. Careful adjustment of the gate electrode bias and balance to earth is required to ensure that negligible spurious signals are produced in the resonant circuit within a given bandwidth which may, for example, be as mentioned above.

The switching pulse required by the FETs is several volts and must be reduced to considerably less than a microvolt to prevent leakage into the resonant circuit. If a square pulse were used considerable voltage components would occur for example in the bandwidth mentioned above and these components could not be entirely removed by balancing. For this reason the switching pulse is shaped as shown in FIG. 7 with an abrupt leading edge 40 and an approximately exponential trailing edge 41 preferably having a substantially constant rate of change which does not give rise to significant components within a required bandwidth. In the examples shown a negative going rectangular pulse of duration about 500 microseconds is applied to the non-inverting input of an operational amplifier 230 with output connected to a pulse shaping circuit comprising a 500 Ohm resistor 231, a 10 kOhm resistor 232, a 6800 pF capacitor 233 and a diode 234. The rise time of the resultant pulse is determined by the resistor 231 and the diode 234 and the exponential decay by the resistor 232 and the capacitor 233. The values of these components are chosen empirically but they are not critical. The output from the pulse shaping circuit is passed by way of an operational amplifier 236 connected as a buffer and a variable resistor 237 which enables the amplitude of the pulses to be adjusted as required.

Capacitive coupling between the windings 21 and 26 and the winding 12 of the inductor causes an additive component from switching transients and must therefore be eliminated as far as possible. In this example the windings 21 and 26 are each wound with a thin coaxial cable, the outer of which is earthed at one point. Further these windings are wound over the whole length of the winding 12 to reduce magnetic field leakage.

The waveform generator of the present invention can be used to generate bursts of oscillations in many resonant circuits having a wide variety of applications in addition to the resonant circuit of the above described NMR apparatus.

We claim:

1. A waveform generator for a high Q resonant circuit to generate in the resonant circuit oscillations having an envelope which rises in magnitude linearly to a maximum and then immediately decays linearly to zero, comprising means for generating pulses formed by bursts of oscillations, each pulse having a rectangular envelope and two contiguous portions with a phase change of 180° at the junction of the two portions, means for adjusting the amplitude of one of the portions of each pulse, and means for adjusting the duration of the same or the other portion of each pulse.

2. A generator according to claim 1 wherein the means for generating pulses generates bursts of sinusoidal oscillations.

3. A generator according to claim 1 wherein the means for generating pulses generates bursts in which the initial phase of each successive burst of oscillations in a sequence of bursts is changed by 180° relative to the initial phase of the previous burst.

4. A generator according to claim 3 wherein the means for generating pulses generates a first pulse in each sequence which has half the maximum amplitude of succeeding pulses.

5. A generator according to claim 3 wherein the means for generating pulses comprises
   supply means for supplying an oscillating signal,
   inverter means coupled to the supply means,
   first and second groups of switch means coupled to the supply means and the inverter means,
   combining means for combining the outputs of the groups of switching means, and
   means for so supplying switching pulses to the switching means that sequences of pulses of the required relative phase appear at the output of the combining means.

6. Nuclear magnetic resonance apparatus comprising first and second means for generating opposed magnetic fields in a space containing a solenoidal first winding having its axis aligned with the fields and containing a core of magnetic material, reactive impedance connected across the first winding to form a high Q resonant circuit, waveform-generation means for generating pulses formed by bursts of oscillations and for applying the pulses to the first winding, each pulse having a rectangular envelope and two contiguous portions with a phase change of 180° at the junction of the two portions, means for adjusting the amplitude of one of the portions of each pulse, means for adjusting the duration of the same or the other portion of each pulse, and means for deriving signals representative of signals induced in the first winding between the bursts.

7. Apparatus according to claim 6 wherein the means for generating pulses generates bursts of sinusoidal oscillations in which the initial phase of each successive burst of oscillations in a sequence of bursts is changed by 180° relative to the initial phase of the previous burst and the first pulse in each sequence has half the maximum amplitude of succeeding pulses.

8. Apparatus according to claim 7 wherein the means for generating pulses comprises
supply means for supplying an oscillating signal,
inverter means coupled to the supply means,
first and second groups of switch means coupled to the supply means and the inverter means,
combining means for combining the outputs of the groups of switching means, and
means for so supplying switching pulses to the switching means that sequences of pulses of the required relative phase appear at the output of the combining means.

9. A method of generating oscillations in a resonant circuit having an envelope which rises in magnitude linearly to a maximum and then immediately decays linearly to zero, comprising the steps of generating pulses formed by bursts of oscillations, each pulse having a rectangular envelope and two contiguous portions with a phase change of 180° at the junction of the two portions, and adjusting both the amplitude of one of the portions of each pulse and the duration of the same or the other portion of each pulse to ive the required linear decay to zero.

* * * * *